(12) United States Patent
Schouenborg et al.

(10) Patent No.: US 8,751,014 B2
(45) Date of Patent: Jun. 10, 2014

(54) DISPLACEMENT RESISTANT MICROELECTRODE, MICROELECTRODE BUNDLE AND MICROELECTRODE ARRAY

(75) Inventors: Jens Schouenborg, Lund (SE); Gustav Lind, Lund (SE); Christopher Hirst, Sjöbo (SE); Lars-Åke Clementz, Lund (SE)

(73) Assignee: Neuronano AB (SE)

( * ) Notice: Subject to any disclaimer, the term of this patent is extended or adjusted under 35 U.S.C. 154(b) by 0 days.

(21) Appl. No.: 13/818,945

(22) PCT Filed: Aug. 25, 2011

(86) PCT No.: PCT/EP2011/064641
§ 371 (c)(1),
(2), (4) Date: Mar. 6, 2013

(87) PCT Pub. No.: WO2012/025596
PCT Pub. Date: Mar. 1, 2012

(65) Prior Publication Data
US 2013/0190851 A1    Jul. 25, 2013

(30) Foreign Application Priority Data
Aug. 25, 2010 (SE) ........................................ 1000862

(51) Int. Cl.
*A61N 1/00* (2006.01)
*A61B 5/04* (2006.01)

(52) U.S. Cl.
USPC ........................................ 607/116; 600/373

(58) Field of Classification Search
USPC ........................................ 607/116; 600/373
See application file for complete search history.

(56) References Cited

U.S. PATENT DOCUMENTS

| | | | |
|---|---|---|---|
| 3,724,467 A | 4/1973 | Avery et al. | |
| 3,822,708 A | 7/1974 | Zilber | |
| 3,995,560 A | 12/1976 | Mackintosh | |
| 4,379,462 A | 4/1983 | Borkan et al. | |
| 4,427,483 A | 1/1984 | Sachs | 156/345 |
| 4,573,481 A | 3/1986 | Bullara | |
| 4,852,573 A | 8/1989 | Kennedy | |
| 4,920,979 A | 5/1990 | Bullara | |
| 5,031,621 A | 7/1991 | Grandjean et al. | |
| 5,215,008 A | 6/1993 | Kartovaara et al. | |

(Continued)

FOREIGN PATENT DOCUMENTS

| | | |
|---|---|---|
| WO | WO 2007/040442 | 4/2007 |
| WO | WO 2008/091197 | 7/2008 |
| WO | WO 2009/075625 A1 | 6/2009 |
| WO | WO 2009/149197 A2 | 12/2009 |

OTHER PUBLICATIONS

International Search Report dated Feb. 29, 2012 issued in corresponding International Patent Application No. PCT/EP2011/064641.

(Continued)

*Primary Examiner* — Nicole F Lavert
(74) *Attorney, Agent, or Firm* — Ostrolenk Faber LLP

(57) ABSTRACT

A medical microelectrode has a front end, a rear end and a density at 20° C. of from 0.80 to 1.15. The electrode comprises any of: electrically conductive tubiform lead comprising a metal and/or an electrically conductive polymer, the lead having an outer surface and a sealed lumen; electrically conductive wire lead comprising a metal and/or an electrically conductive polymer, the lead having a surface and a buoyant element of a density of less than 1.0 attached to the surface.

30 Claims, 4 Drawing Sheets

(56) References Cited

U.S. PATENT DOCUMENTS

| | | |
|---|---|---|
| 5,417,719 A | 5/1995 | Hull et al. |
| 5,501,703 A | 3/1996 | Holsheimer et al. |
| 5,741,319 A | 4/1998 | Woloszko et al. |
| 5,957,958 A | 9/1999 | Schulman et al. |
| 6,032,062 A | 2/2000 | Nisch |
| 6,253,110 B1 | 6/2001 | Brabec et al. |
| 6,421,566 B1 | 7/2002 | Holsheimer |
| 6,993,392 B2 | 1/2006 | Nicolelis et al. |
| 7,041,492 B2 | 5/2006 | Oka et al. |
| 7,099,718 B1 | 8/2006 | Thacker et al. |
| 7,146,221 B2 | 12/2006 | Krulevitch et al. |
| 2003/0105505 A1 | 6/2003 | Pianca .......... 607/122 |
| 2007/0197892 A1 | 8/2007 | Shen et al. |
| 2008/0119711 A1 | 5/2008 | Nikumb .......... 600/378 |

OTHER PUBLICATIONS

European Search Report, dated May 24, 2013, issued in corresponding European Application No. EP 13159215.6. Total pages 4.

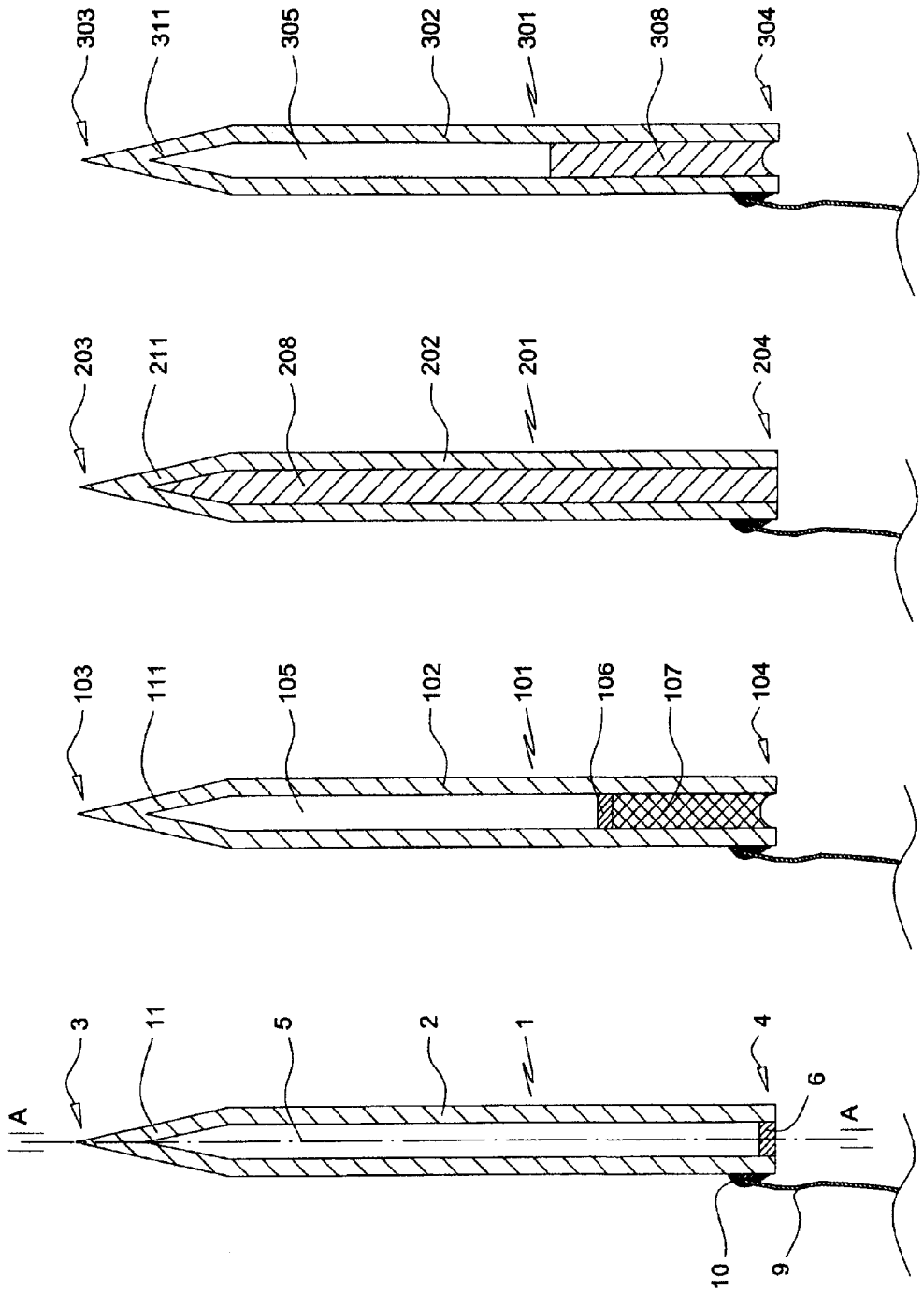

DISPLACEMENT RESISTANT MICROELECTRODE, MICROELECTRODE BUNDLE AND MICROELECTRODE ARRAY

CROSS REFERENCE TO RELATED APPLICATIONS

The present application is a 35 U.S.C. §371 National Phase conversion of PCT/EP2011/064641, filed Aug. 25, 2011, which claims benefit of Swedish Application No. 1000862-1, filed Aug. 25, 2010, the disclosure of which is incorporated herein by reference. The PCT International Application was published in the English language.

FIELD OF THE INVENTION

The invention relates to a medical microelectrode, to a bundle of microelectrodes, and to an array of microelectrodes and/or microelectrode bundles. The microelectrode, microelectrode bundle and array of microelectrodes or microelectrode bundles of the invention are intended for insertion into soft tissue such as the brain, the spinal cord, endocrine organs, muscles, and connective tissue. The medical microelectrode, the bundle of microelectrodes, and the array of microelectrodes and/or microelectrode bundles are designed to resist displacement in the tissue.

BACKGROUND OF THE INVENTION

Microelectrodes that can be implanted for a long time into the central nervous system (CNS) have a wide field of application. In principle, all brain nuclei can be recorded from or stimulated by such electrodes and their functions monitored. Of particular importance is the use of a multichannel design in brain nuclei stimulation. In such a design, groups of electrodes or even individual electrodes can be addressed separately. This allows the user to select those electrodes whose stimulation produces a therapeutic effect that is improved in comparison with unselective stimulation. Stimulation of the brain or spinal cord can be of particular value in situations when brain nuclei are degenerated or injured. In certain situations it would also be useful to be able to combine controlled electrical stimulation and localized gene transfer. A multichannel design may also allow the user to effectively measure the effects on multiple neurons and other cells following systemic or local drug administration or gene transfer. Of particular interest is an ability to simultaneously measure the effects of multiple drug candidates on neuronal function. Monitoring brain activity through implanted electrodes can also be useful if used to control drug delivery either locally or systemically or other therapeutic methods such as electrical stimulation of brain nuclei. Multichannel electrodes may also be used to lesion specific and circumscribed sites in tissue after abnormal impulse activity has been detected by recordings from the electrodes.

To record and stimulate brain structures various forms of implantable electrodes have been developed (U.S. Pat. No. 6,253,110 B1, U.S. Pat. No. 5,957,958, U.S. Pat. No. 4,573,481, U.S. Pat. No. 7,146,221 B2, U.S. Pat. No. 5,741,319, U.S. Pat. No. 4,920,979, U.S. Pat. No. 5,215,008, U.S. Pat. No. 5,031,621, U.S. Pat. No. 6,993,392 B2, U.S. Pat. No. 6,032,062, U.S. Pat. No. 4,852,573, U.S. Pat. No. 3,995,560, U.S. Pat. No. 7,041,492, U.S. Pat. No. 6,421,566 B1, U.S. Pat. No. 4,379,462, U.S. Pat. No. 5,417,719, U.S. Pat. No. 3,822,708, U.S. Pat. No. 5,501,703, U.S. Pat. No. 7,099,718 B1, U.S. Pat. No. 3,724,467; US 2007/0197892 A1).

For the function of an electrode implant it is important to have a fixed spatial relationship between the recording/stimulation sites on the implant and the measured entities. The body and thus the tissue exhibit considerable movements during daily life. Movements are caused by for example respiration, the heart beat, intestinal movement, skeletal movements such as rotating the head in relation to the body. Movements may also be caused by external forces on the body. Relative movements between tissue and electrodes can cause changes in the recorded biological signals such as electrical or chemical signals such as transmitter substances. For example, an action potential corresponds to a voltage change in the order of 100 mV over the neuronal membrane. This potential change fades quickly with distance from the cell. Consequently, movements of the electrode relative to a measured cell can result in a considerable variation in the amplitude of the measured action potential. Likewise, when the electrodes are used for electrical stimulation, a shift in location of the electrode relative to the tissue may result in a shift of the neurons stimulated. It is thus very important that the sites on the medical electrode from where recordings or stimulations are made in the tissue can follow the movements of the tissue in which it is embedded as faithfully as possible. Besides impairing the recorded signal or efficacy of stimulation, movements between implants and tissue may cause injuries to the tissue that in turn can trigger a tissue reaction and loss of function of the implant. Mechanical stability between electrode and tissue is particularly important for intracellular recordings because movements of electrode relative to the cell can easily damage the membrane and cause leakage of extracellular fluid into the cell and vice versa. Today there is no known electrode implants designed or suitable for intracellular recordings simultaneously in many neurons over long time spans such as days, weeks or months in freely moving animals or humans.

Ultra thin electrodes that are flexible and thereby overcome some of the problems related to movements between tissue and electrode are known in the art (WO 2007/040442). By embedding such electrodes in a dissolvable hard matrix it is possible to implant them in soft tissue, without any additional support such as a syringe. Such ultrathin electrodes should be made of a material that is not degraded by the tissue or easily oxidized causing high electrical resistance and thereby decreased signal to noise ratio. Examples of suitable conductors are noble metals such as gold and platinum. Commonly an alloy of platinum and iridium is used as a material for implants used for stimulation.

To achieve a physically stable contact with cells in the nervous system it is also important that the electrode is anchored in the tissue close to the measured or stimulated tissue. Electrodes with electrically conducting barbs and electrode sheets equipped with holes through which the tissue may grow and thereby attach firmly to the electrode are known in the art (WO 2007/040442; WO 2008/091197; WO 2009/075625). However, implants may cause chronic inflammation and even infections and may have to be removed. In the situation when the electrode is withdrawn from the tissue anchoring devices known by the art such as barbs or in particular holes in the electrode body allowing tissue ingrowth may cause extensive damage to the tissue. It is thus desirable to solve the problem of how to anchor a medical electrode in soft tissue such that the medical electrode is physically stabilized in the tissue and yet can be withdrawn from the tissue with reduced tissue damage.

OBJECTS OF THE INVENTION

It is an object of the invention to provide a microelectrode that is stabilized against displacement within the tissue into which it has been implanted.

It is another object of the invention to provide a microelectrode bundle comprising such electrode(s).

It is a further object of the invention to provide a microelectrode array and a microelectrode bundle array comprising such electrode(s).

Further objects of the invention will become apparent from the following summary of the invention, a number of preferred embodiments thereof illustrated in a drawing, and the appended claims.

SUMMARY OF THE INVENTION

The present invention is based on the insight that, to optimally resist displacement within soft tissue to which has been implanted, a microelectrode should approximate the specific weight of the tissue. By such approximation, the electrode is "floating" in the tissue, and may be termed floating microelectrode. The floating property of the electrode makes it follow the displacement of the surrounding tissue when the tissue is accelerated or decelerated. The stabilization according to the invention thus is one against displacement within a tissue, in contrast to stabilization against withdrawal from tissue by mechanical anchoring means, such as barbs, spikes, and the like. It is, of course, feasible to provide the electrode of the invention additionally with such means against withdrawal from tissue. Stabilization according to the invention is particularly useful for electrodes implanted into delicate non-fibrous soft tissue, such as tissues of the brain, the spinal canal, and bone marrow.

The microelectrode of the invention is intended for recording electrical signals arising in the tissue, in particular nervous tissue, but may also be used for electrical stimulation of tissue.

Thus, according to the present invention is disclosed a medical microelectrode resistant to displacement in soft tissue by inertia.

The electrode comprises an electrically conductive tubiform lead comprising or consisting of a metal and/or an electrically conducting polymer. The tubiform lead has an outer face and an inner face. The outer face of the tubiform lead may be porous but not in a manner permitting penetration of aqueous body fluid into the lumen. Thus the pores either do not penetrate the outer face or are sealed at a desired depth, for instance by applying a polymer coat in the inner luminal surface of the tubiform lead. The tubiform lead has a front or distal end, a rear or proximal end, and a sealed lumen disposed between the front end and the rear end. The lumen of the tubiform lead is void or comprises one or more void sections and one or more sections partially or fully filled with filler. The density at 20° C. of the filler is preferably 0.8 or less, in particular 0.6 or less. Advantageously the filler comprises or consists of a porous material, in particular a porous material with closed pores. It is preferred for filler to consist of or comprise a polymer, in particular of a polymer with closed pores. The polymer is preferably flexible, in particular resiliently flexible.

Alternatively, the electrode comprises or consists of a wire lead. The wire lead may be porous or non-porous. In the embodiment in which the lead is a wire lead the insulation on the lead can be of a porous polymer material comprising sealed pores, that is, pores that do not soak up body fluid. Alternatively, on a thin, non-porous insulating layer on the wire lead is disposed a porous polymer material comprising sealed pores. The volume of the porous insulating material is selected to as to compensate for the high density of the metal wire lead.

The density of the electrode at a temperature of 20° C. is preferably from 0.80 to 1.15, more preferred from 0.90 to 1.07, even more preferred from 0.95 to. 1.03 most preferred 0.99±0.02. Optionally a portion of the outer face of the electrode is electrically insulated. Leads of a cylindrical or elliptical transverse section are preferred, but leads of other kind of transverse sections, such as triangular, square or hexagonal, are not excluded from the invention. In this application, an oblong lead is one of a length/diameter ratio of 5 or more, in particular of 10 or more, most preferred of 20 or more. A preferred lead diameter is from 1 μm to 200 μm. The lead is preferably of a metal selected from gold, silver, platinum and copper or of an alloy comprising one or more of these metals. Alternatively the lead is of an electrically conducting modification of carbon such as carbon nanotubes or of an electrically conducting polymer. The lead may also comprise a combination of such materials.

According to a preferred aspect of the invention the electrode is fully or partially embedded in a matrix dissolvable or degradable in a body fluid.

According to another preferred aspect of the invention the electrode comprises an electronic amplifying means and/or a microprocessor means, with the proviso that the combination of electrode and electronic amplifying means/microprocessor means has a density at 20° C. of from 0.80 to 1.15, in particular from 0.90 to 1.07, more particularly from 0.95 to 1.03, and even 0.99±0.02. It is preferred for the electronic amplifying means/microprocessor means to be disposed at or near the rear end of the electrode.

Alternatively is provided an electronic amplifying and/or microprocessor means separate of the electrode implanted in the tissue. Electrical communication between the electrode and the electronic amplifying/microprocessor means disposed at a distance from the electrode is provided by an insulated electric conductor such as by an ultra-thin insulated wire mounted at or near the rear end of the electrode at the one hand and at the electronic amplifying/microprocessor means at the other hand; a preferred thickness of the wire is 50 μm or less. It is preferred for the conductor to be of about the same density as that of the electrode, that is, of a density of about 1, in particular of from 0.9 to 1.1. The density of the electrical conductor of wire type can be controlled by providing it with a buoyancy element of a density of <1 such as, for instance, a spongy polymer insulating coat. It is also preferred for the electronic amplifying/microprocessor means separate of the electrode to be of about the same density as that of the electrode, that is, a density of about 1, in particular of from 0.9 to 1.1. The electronic amplifying/microprocessor means of the electrode can be powered by, for instance, a power source, such as battery implanted in tissue or external of it; electrical connection between the power source and the electronic amplifying/microprocessor means of the electrode being provided by an electrical conductor of the aforementioned kind made buoyant by providing it with an buoyancy element.

Microprocessor means separate of the electrode are preferably disposed in soft tissue of said person or animal but may also be disposed externally of said person or animal. The amplifying/microprocessor means may comprise a source of electric energy such as a battery or be connected to an external source by an electrical lead. The amplifying/microprocessor means may also comprise a means for transmitting and/or receiving radiation to/from a control unit disposed externally of the patient or animal. The electrode of the invention is capable of electric communication with microprocessor means disposed at a distance therefrom in the tissue of the person or animal or externally thereof. The microprocessor means may comprise a source of electric energy, such as a LiH cell. The microprocessor may also comprise a means for transmitting and/or receiving radiation to/from a control unit disposed externally of said patient or animal.

According to another preferred aspect of the invention the electrode may comprise anchoring means disposed at or near its front end, preferably integral with the electrode lead. Since the electrode of the invention is not easily dislocated by a sudden displacement of the tissue in which it is embedded, the need for anchoring it in the tissue is less pronounced than with traditional microelectrodes of a density substantially higher than 1. A rough electrode surface or a rough portion thereof, such as a rough electrode tip, may suffice for anchoring.

According to a further preferred aspect, the electrode may be of a porous, electrically conducting material or comprise such material. Preferred porous, electrically conducting materials are sintered metal powders, in particular of titanium, aluminum, and their alloys. Other porous, electrically conducting materials comprise or consist of carbon nanotubes and/or fullerenes and/or thin sheets of graphite down to graphite mono-layers. The pores of such materials opening at the surface of the electrode can be sealed by, for instance, electrically insulating materials such as polyurethane or polyimide coatings or, at non-electrically insulated portion(s) of the electrode, by electrically conducting materials such as by electrolytically deposited layers of gold or other noble metals.

Alternatively the electrode may comprise a porous, electrically non-conducting material. Preferred porous, electrically non-conducting materials include porous organic polymers, such as porous polyurethane, and porous ceramic materials, such as sintered alumina, on which an electrically conducting layer comprising or consisting of a metal or metal alloy has been deposited by, for instance, ion sputtering.

The pores of the porous electrically-conducting or non-conducting material of the electrode of the invention may be open or closed. If open, they are protected from intrusion of aqueous body fluids by sealing with, for instance, non-conducting lacquers or thin metal layers deposited thereon by ion sputtering or other suitable techniques. In order to provide the entire electrode with the preferred density of the invention at 20° C. of from 0.80 to 1.15, in particular from 0.90 to 1.07, more particularly from 0.95 to 1.03, and even 0.99±0.02 the porosity of the porous electrically-conducting or non-conducting material of the electrode is dimensioned so as to fully or at least substantially partially compensate for the density of >1 of the bulk electrode material. To achieve the preferred density, porous electrode materials of the invention can be advantageously combined with the electrodes having a sealed lumen and/or comprising a buoyant element attached to their surface.

According to the present invention is also disclosed an electrode bundle comprising two or more electrodes of the invention. The electrode bundle comprises a non-permanent bundling means, preferably in form of a material dissolvable or degradable in a body fluid in which the two or more electrodes are enclosed in a substantially parallel configuration. Consequently, a electrode of the invention can be comprised by such an electrode bundle. It is preferred for the electrode bundle to have a density at 20° C. of from 0.80 to 1.15, in particular from 0.90 to 1.07, more particularly from 0.95 to 1.03, and even of 0.99±0.02.

According to a further preferred aspect of the invention is disclosed an electrode lead comprising multiple electrically conductive layers interspaced with non-conductive layers of low density polymer material; such leads can be manufactured by electrospinning, for instance gold nanowires spun in parallel with or around low density polymer fibres. Fusing the ends of the lead by means of laser radiation or any other suitable heat source establishes electric contact between the electrically conductive layers to make them constitute a single electrode lead.

The electrode of the invention may furthermore comprise useful features known from state-of-the-art microelectrodes.

According to the present invention is furthermore disclosed an electrode array comprising two or more electrodes and/or electrode bundles of the invention. According to an advantageous aspect of the invention the electrode array is partially or fully enclosed in a material dissolvable or degradable in a body fluid. It is preferred for the electrode array to have a density at 20° C. of from 0.80 to 1.15, in particular from 0.90 to 1.07, more particularly from 0.95 to 1.03, and even of 0.99±0.02. Consequently, an electrode of the invention can be comprised by such an electrode array.

Embedment of the electrode of the invention in a material intended to be dissolved or degraded upon implantation of the electrode allows a tiny and flexible microelectrodes and bundles and arrays comprising them to be inserted into tissue without putting their integrity at risk.

The electrode embedding material is disregarded from when considered determining the density of the electrode of the invention.

According to another important aspect, the invention teaches that, in addition to the entire electrode being designed so as to its density approach that of soft tissue, that is, about 1.0, it is important to design the electrode in a manner so as to distribute elements of high density and elements of low density over the entire electrode as evenly as possible. Most often, the electrode of the invention will be oblong; in an oblong electrode configuration it is thus advantageous to compensate for density deviations along the electrode. This kind of compensation avoids preferred orientation of portions of the electrode in the tissue by the effect of gravity, such as, for instance, of an electrode of the invention having a front end section of relatively high density pointing downwards in a state flowing in the tissue and a rear section of relatively low density pointing upwards in the same state, or vice-versa. Elements of high density comprise metallic electrode leads, micro signal amplifiers or other electronic gear attached to the electrode lead at its rear end, etc.; elements of low density comprise buoyancy elements disposed on the electrode lead or voids in the electrode lead. Of major importance is also the proper selection of materials, in particular of metallic materials including composites comprising metals for electrode leads. Thus, it is preferred for the electrode of the invention to be density-balanced. By "density-balanced" is understood that not only are high-density portions of the electrode balanced by low-density portions so as to achieve a electrode of desired density in total but that the balancing of density is localized to portions of the electrode in need of balancing. A measure of balancing an electrode of the invention is the distance between its center of gravity ($C_g$) and the center of gravity ($C_{g'}$) of an identically shaped electrode of uniform density. In a balanced electrode of the invention having a front end and a rear end spaced apart by a distance L, the distance I between said centers of gravity $C_g$, $C_{g'}$ is less than 25% of the distance L, preferably less than 15%, most preferred less than 10%.

According to the present invention is also disclosed an electrode bundle and an electrode array comprising one or more electrodes of the invention. An electrode bundle comprises two or more electrodes of the invention bundled by a bundling means that may be permanent or temporary. "Permanent" and "temporary" relate to a state of the electrode bundle upon implantation. A permanent bundling means is one designed for preserving the integrity of the bundle during the period of electrode use in the tissue, whereas a temporary bundling means is one designed for preserving such integrity during insertion of the bundle into the tissue but not during the period of electrode use in the tissue. A permanent bundling means comprises, for instance, a girth or sleeve enclosing two or more electrodes of the invention disposed in parallel near their rear ends, which girth or sleeve is not easily dissolved or degraded by a body fluid. A temporary bundling means comprises, for instance, a glue connecting at least rear portions of electrodes so disposed near their rear ends, the glue being dissolvable in a body fluid.

For easy implantation, the electrode bundle and the electrode array of the invention can be partially or fully enclosed by a material dissolvable or degradable in a body fluid. This kind of enclosure can also fulfill the function of the temporary electrode bundling means of the invention. A partial enclosure does at least enclose the front portions of the electrodes of the electrode bundle or the electrode bundle array.

The invention will now be described in more detail by reference to a number of preferred embodiments illustrated in a drawing. FIGS. 1-11 of the drawing are not to scale but only intended to clearly illustrate principal features of the invention.

BRIEF DESCRIPTION OF THE DRAWINGS

FIG. 1 shows a first embodiment of the electrode of the invention in an axial (A-A) section;
FIGS. 1-8 show variations of the embodiment of FIG. 1, in the same view.

DESCRIPTION OF PREFERRED EMBODIMENTS

Figure 8:
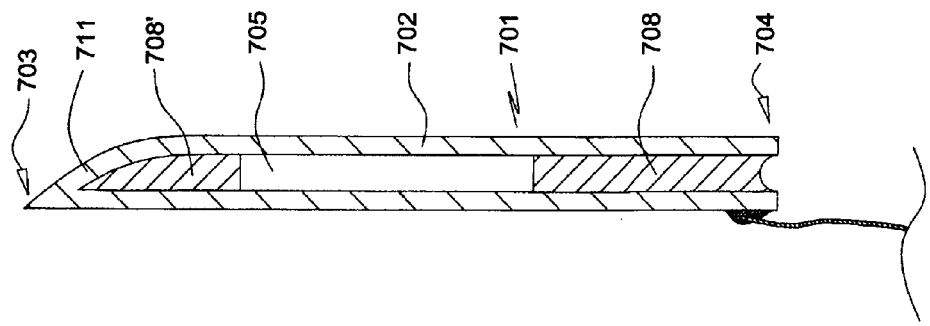

A first embodiment of the medical microelectrode 1 illustrated in FIG. 1 comprises an electrically conductive tubiform lead 2 of silver alloyed with 20% of copper. At its front end 3 the lead 2 is closed and has a sharp point 11. At its rear end 4 the lumen 5 of the lead 2 is sealed by a polyethylene plug 6 disposed in the lumen 5 at the rear end 4. A thin insulated (not shown) metal wire 9 is conductively attached by solder 10 to the outer surface of the lead 2 at the rear end 4 thereof. The wire 9 connects the electrode 1 to an electrode control unit (not shown) comprising microprocessor means.

In a first variation 101 of the microelectrode of FIG. 1 illustrated in FIG. 2 a polyethylene plug 106 is disposed in the lumen 105 at a distance from the rear end 104 of the pointed 111 lead 102 of an aluminum alloy so as to divide the lumen 105 at a ratio of about 2:1 in a sealed portion extending from plug 104 towards the front end 103 and an open portion extending from the plug 104 towards the rear end 104. The open portion of the lumen 105 is filled with compressed glucose powder 107. Upon insertion of the electrode 101 into soft tissue aqueous body fluid contacts the powder 107 and slowly dissolves it. Filling the open portion of the lumen 105 with a material dissolvable in an aqueous fluid avoids a pocket filled with air to remain in the open portion of the lumen 105.

In a second variation 201 of the microelectrode of FIG. 1 illustrated in FIG. 3 the entire lumen of the pointed 211 electrode lead 202 of a gold/silver alloy extending from the closed front end 203 to the open rear end 204 is filled with polyurethane foam 208 with closed pores.

The third variation 301 of the microelectrode of FIG. 1 illustrated in FIG. 4 differs from the variation of FIG. 3 in that only a rear-end 304 portion of the lumen 305 is filled with polyurethane foam 308. The front-end portion of the lumen 305 is thereby sealed and remains void. Again, the electrode lead 302 is pointed 311 at its front end 303 and open at its rear end 304.

The fourth microelectrode variation 401 illustrated in FIG. 4 differs from of the microelectrode of FIG. 1 by the front end 403 of the lead 402 having a blunt tip 411. At the rear end 404 the lumen 405 is closed by a polyethylene plug. 406. A thin insulated (not shown) wire 409 soldered (at 410) to the outer surface of the lead 402 provides electrical communication between the electrode 401 and an electrode control unit (not shown).

Figure 6:
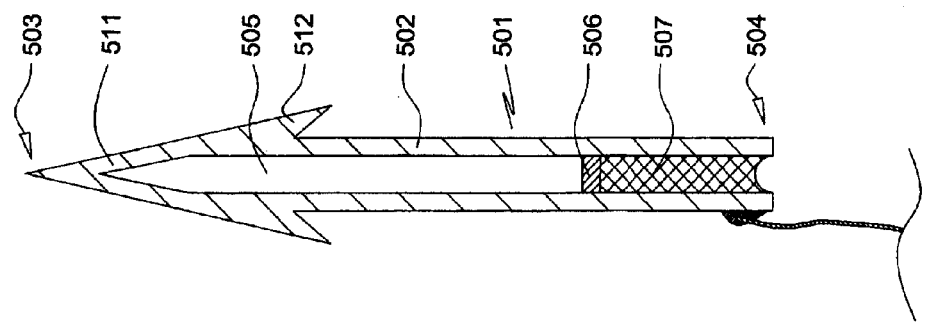
Figure 5:
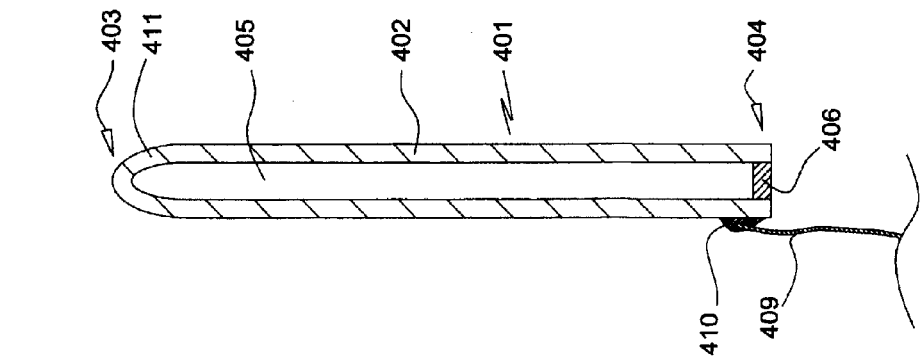

The fifth variation 501 of the microelectrode of FIG. 1 illustrated in FIG. 6 differs from the microelectrode of FIG. 2 by its tip 511 being provided with anchoring means in form of barbs 512 for securing the electrode, once inserted into soft tissue, from being accidentally withdrawn. Reference numbers 502, 503, 504, 506, 507 identify elements corresponding to those numbered 202, 203, 204, 206, 207 in FIG. 2.

Figure 7:
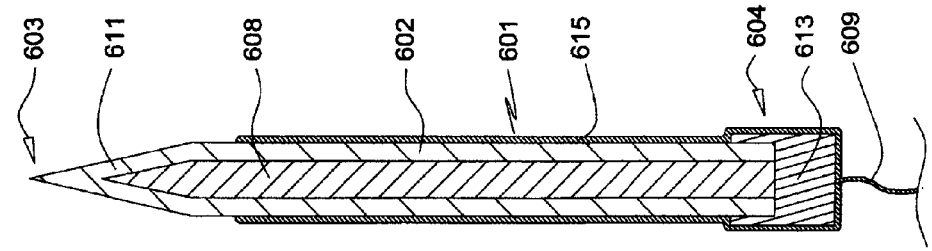

The sixth variation 601 of the microelectrode of FIG. 1 illustrated in FIG. 7 comprises a tubiform platinum alloy lead 602 closed at its front end 603 by a pointed tip 611 and open at its rear end 604. The lumen is filled with polymer foam. At its rear end the lead 602 is provided with a signal amplifier 613 from which an insulated ultra-thin wire 609 extends. The wire 609 provided electrical connection of the signal amplifier 613 with an electrode control unit (not shown). Except for its pointed front-end 603 tip the lead 602 and the signal amplifier 613 are encapsulated by an electrically insulating lacquer 615.

The seventh variation 701 of the microelectrode of FIG. 1 illustrated in FIG. 8 comprises a tubiform lead 702 which is rotationally symmetric except for its front-end 603 pointed tip 711. The lumen 702 is partially filled with polymer foam, a first foam section 708 extending from the rear end 704 of the lead 702 towards the front end 703 and a second foam section 708' extending from the front end 703 towards the rear end 704 so as to delimit a void central section 705 of the lead lumen.

Figure 9:
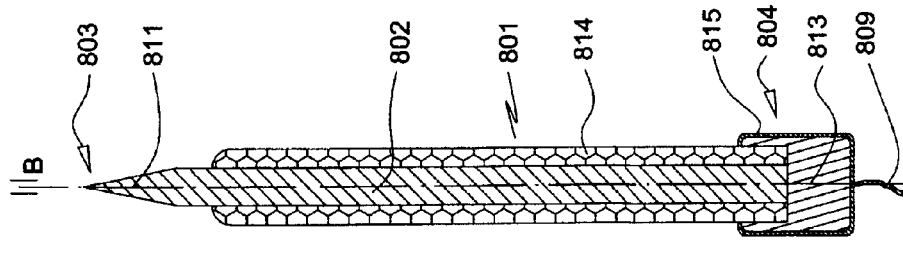
FIG. 9 shows a second embodiment of the electrode of the invention in an axial (B-B) section.

A second embodiment 801 of the medical microelectrode of the invention illustrated in FIG. 9 comprises a solid electrode lead 802 of titanium having a front end 803 and a rear end 804, the front end 803 being provided with a pointed tip 811. Except for at its tip 811 the lead 802 is enclosed by a buoyant layer 814 of polymer foam with closed pores, which abuts the lead 802 and firmly adheres to it. The buoyant layer 814 has substantially the form of a sleeve on the lead 802. At the rear end of the lead 802 an electrode signal amplifier 813 is disposed, which is sealed by a thin layer 815 of lacquer. The amplifier 813 is in electrical communication with an electrode control unit (not shown) by an insulated ultra-thin metal wire 809.

Figure 10:
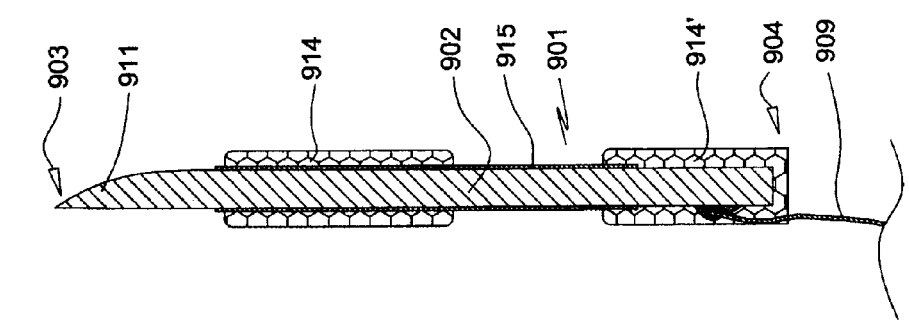
FIG. 10 shows a variation of the embodiment of FIG. 9, in the same view.

A variation 901 of the second embodiment of the medical microelectrode of the invention is illustrated in FIG. 10. The buoyant layer comprises two sections 914, 914' spaced apart, the first section 914 disposed near the front end 903 and the second section 914' disposed near the rear end 904 of the electrode lead 902 of tungsten. The surface of the lead 902 extending between the sections 914, 914' is insulated by a lacquer 915. Thus, only the rotationally asymmetric tip 911 is not insulated. At its rear end the electrode 901 has an ultrathin electrically insulated wire 909 soldered to it, which provides for electrical communication with an electrode control unit (not shown) disposed at a distance from the electrode 901 intra- or extra-corporeally.

Figure 11:
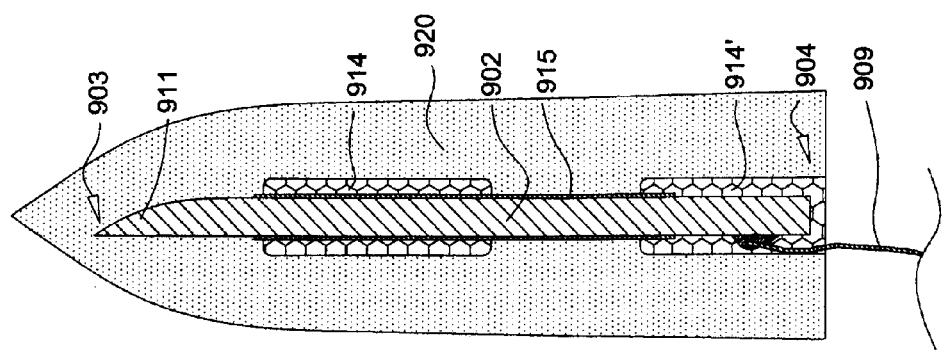
FIG. 11 shows the electrode of FIG. 10 embedded in dissolvable matrix body.

FIG. 11 shows the electrode of FIG. 10 incorporated into a body of a carbohydrate matrix 920 by which the tiny electrode 901 can be inserted into soft tissue without jeopardizing its physical integrity. Upon insertion the matrix body 902 is dissolved by aqueous body fluid so as to establish physical contact of the electrode with the tissue. The matrix body 920 is rotationally symmetric and so arranged around the electrode 901 to make its axis of rotation coincide with that of the electrode 901. At its front end the matrix body 920 has a pointed tip 921.

Dimensioning of Electrodes of the Invention

Radial dimensioning of electrodes of the invention so as to have their density approach 1.0 is illustrated below in a number of examples. The outer diameter of the electrodes is set to 100 µm. Radial dimensions of thicker or thinner electrodes are obtained by multiplying the thickness of the electrode layers by the desired size factor. In the Examples the axial length of the electrode tip is assumed to be negligible in relation to the total length of the electrode lead.

Example 1

Figure 12A:
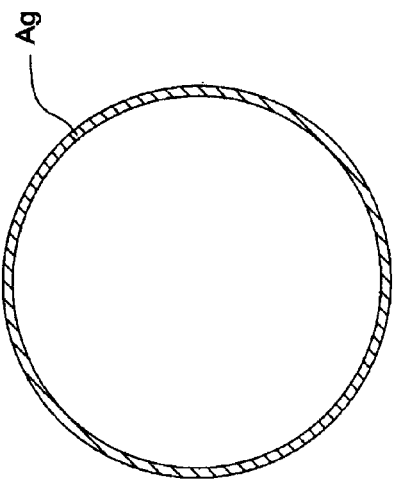
FIGS. 12a-12f show examples of electrode leads of the invention in radial section.

Tubiform silver lead, FIG. 12a; $d_{Ag}$=10.4. Inner (lumen) diameter: 95 µm. Density (calculated): 1.01.

Example 2

Figure 12B:
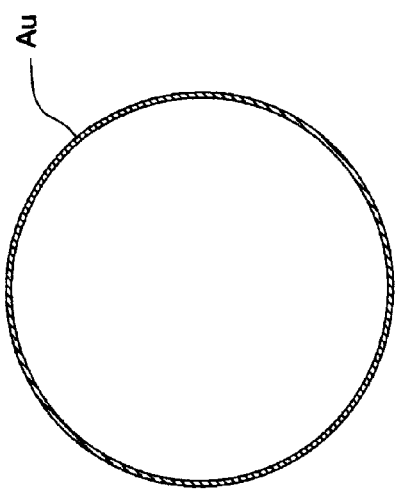

Tubiform gold lead, FIG. 12b; $d_{Au}$=19.3. Inner (lumen) diameter: 97.3 µm. Density (calculated): 1.03.

Example 3

Figure 12C:
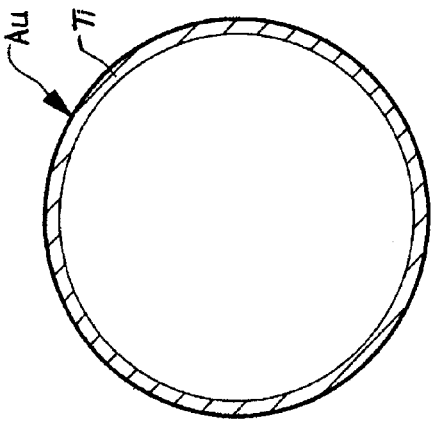

Tubiform bilayer lead, FIG. 12c. Outer layer gold, $d_{Au}$=19.3, inner layer titanium, $d_{Ti}$=4.5. Inner (lumen) diameter: 92 µm; thickness of titanium layer: 7 µm; thickness of gold layer: 1 µm. Density (calculated): 0.986.

Example 4

Figure 12D:
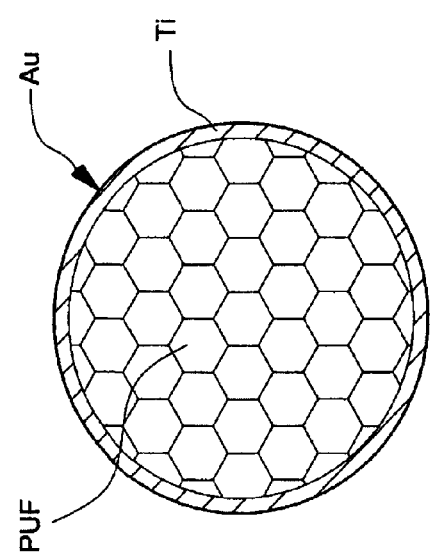

Tubiform bilayer lead, FIG. 12d. Outer layer gold, $d_{Au}$=19.3, inner layer titanium, $d_{Ti}$=4.5. Inner (lumen) diameter: 92 µm; thickness of titanium layer: 7.5 µm; thickness of gold layer: 0.5 µm. Lumen filled with polyurethane foam, $d_{PUF}$=0.20. Density (calculated): 0.963.

Example 5

Figure 12E:
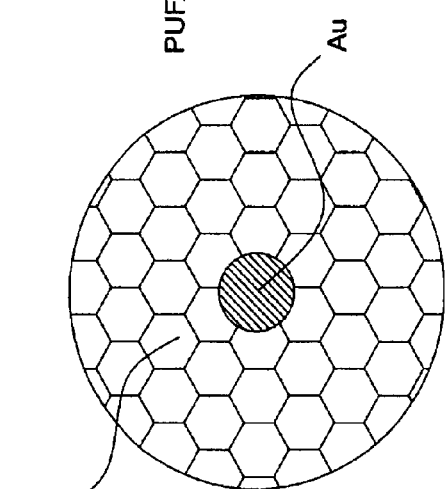

Gold wire lead covered with polyurethane foam with closed pores, FIG. 12e. $d_{Au}$=19.3; $d_{PUF}$=0.24. Diameter of gold wire: 40 µm. Density (calculated): 1.00.

Example 6

Figure 12F:
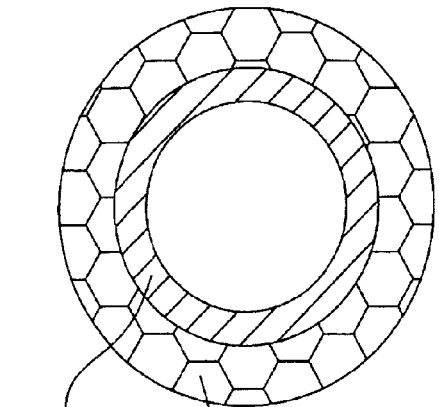

Tubiform titanium lead covered with polyurethane foam with closed pores, FIG. 12f. $d_{Ti}$=4.5; $d_{PUF}$=0.20. Outer diameter of titanium lead: 70 µm; inner (lumen) diameter: 53 µm. Density (calculated): 1.04.

Example 7

Porous nickel lead manufactured by the electroforming method of U.S. Pat. No. 7,393,446 B2 using polystyrene beads about 60 µm in diameter. Outer diameter of the lead: 500 µm. A lead with a density of about 1.1 was produced as one of a series of leads produced by varying the duration of electroforming. Upon formation of the cellular metal structure with open pores the polystyrene matrix is removed by soaking with acetone. The cylindrical porous nickel lead is thoroughly rinsed with acetone, dried, and then electroplated with gold to a plating thickness of about 10µ so as to retain the pores open. The lead is thoroughly rinsed with water, then with acetone, and dried. One end of the lead is cautiously heated with an acetylene burner so as to shrink it to form a blunt tip. To the other end of the lead is attached by soldering a thin insulated copper wire. Except for the shrunken tip portion, the electrode lead is dipped into a solution of polyurethane (Tecoflex® solution grade SG-85A, The Lubrizol Corporation, Cleveland, Ohio) in THF (20%, w/w)) to close the pores and to insulate the main portion of the electrode lead. Other dip-coating materials, such as Thoralon®, for use in the invention comprise polyetherurethane urea containing soft segments made of polytetramethylene oxide and hard segments made of 4.4'-diphenylmethane diisocyanate and ethylene diamine (BPS-215, Thoratec Corporation, Pleasanton, Calif.).

Manufacture of Electrodes of the Invention

Tubiform electrodes of the invention can be manufactured from corresponding metal microtubes. Microtubes of noble metals can be obtained by, for instance, electrolytically coating a less noble metal like aluminum or iron with the noble metal like silver, gold, platinum, etc. but also copper, followed by dissolving the less noble metal by an non-oxidizing strong acid like hydrochloric acid. The front ends of the microtubes can be closed by heating a short portion of the raw tube to slightly below its melting point, then draw its ends in opposite directions at this temperature followed by raising the temperature to the melting point so that a finely drawn out portion collapses. The tube is then drawn apart and two pointed, sharply or rounded, depending on the material and working conditions, microtubes are obtained, which can be cut to a desired length. Alternatively a microtube can be closed at its one end by welding, optionally after flattening the end portion prior to welding. The rear end of microtube closed at its front end can be sealed by, for instance, a slightly conical polyethylene or polypropylene plug which is forced into the open end for a desired distance. Filling the lumen of a microtube with polymer foam is accomplished by injecting a prepolymer solution or suspension in a highly volatile solvent such as propane or butane, followed by gentle heating of the filled microtube. Particulate solid fillers can be poured into the lumen and compressed there by a piston of suitable diameter, if necessary.

Electrically conducting polymers suitable for use in the invention include polyethylenedioxythiophene, polyaniline, polyacetylene, and polypyrrole.

Wire electrodes can be covered with polymer foam by, for instance, arranging them in a closed compartment comprising a receptacle filled with a prepolymer solution or suspension of the aforementioned, dipping them into the solution or suspension, withdrawing them from the solution or suspension, closing the receptacle, admitting air, in particular humid air, to the compartment, storing the so covered electrodes in a humid atmosphere until the polymer is fully cured. The thickness of the layer of polymer with closed pores on the wire can be controlled by controlling the viscosity of the prepolymer solution or suspension and/or the temperature of the solution or suspension in the receptacle and/or the kind of solvent.

Ultra-thin insulation layers can be obtained by applying electrically insulating lacquers to desired portion of the electrode. Alternatively or additionally, insulation coatings of parylene-C can be used, for instance.

Electrodes of the invention comprising porous metal structures can be manufactured, for instance, by methods described in U.S. Pat. No. 7,393,446 B2.

Electrodes of the invention can be bundled or stacked in substantially the same manner as described in WO 2007/040442 A1. Electrodes of the invention can also be incorporated into arrays like those described in WO 2008/091197 A1. Suitable procedures for incorporating electrodes of the invention and electrode bundles and arrays of electrode bundles of the invention into rigid matrix bodies dissolvable in body fluid are disclosed in WO 2009/075625 A1.

Methods of Embedding Microelectrodes of the Invention in a Dissolvable Matrix

A method for embedding the microelectrode of the invention comprises providing a fixation means, fixing the electrode and, optionally, additional elements to be imbedded, such as optical fibres, contractile elements, etc., in the fixation means in a desired configuration, applying a sheath covering the thus fixed electrode and accessories except for at the proximal coupling section thereof, applying a solution or suspension of a first matrix material on the electrode in a manner so as to cover the portions of the electrode intended to be embedded, allowing the solvent/dispersant of the matrix solution or suspension, respectively, to evaporate or harden, removing the sheath, and releasing the electrode from the fixation means. For embedment of the electrode in two matrix materials so as to form corresponding matrix compartments, each enclosing a portion of the electrode, an appropriate portion of the electrode fixed by a fixation means as described above is coated with a solution or suspension of the first matrix material, the solvent/dispersant of which is subsequently evaporated, followed by coating the portion of the electrode remaining to be coated with a solution or suspension of the second matrix material, subsequently evaporating the solvent/dispersant of the second matrix material, and releasing the electrode from the fixation means. In the method the electrode is preferably disposed in a sheath of smooth material of low wettability such as a polyfluorinated hydrocarbon polymer or silicon rubber, and fixed therein. To facilitate solvent evaporation the sheath material is advantageously porous, in particular micro-porous. After application and drying of the matrix material(s), the electrode is withdrawn from the sheath. If desired, a drug or a combination of drugs can be incorporated in the matrix.

An alternative method of embedding an electrode of the invention into two matrix materials forming distinct matrix compartments, comprises embedding the entire electrode in a first matrix material, dissolving a portion of the first matrix material, preferably a distal portion extending from the distal end, covering the now non-embedded distal portion of the electrode with a second matrix material by, for instance, taking recourse to a sheath applied on the non-embedded distal portion, filling the sheath with a solution or suspension of the second matrix material, evaporating the solvent so as to dry/harden the second matrix material, and removing the sheath.

The electrode of the invention can be coated by using a single coating technique or combination of coating techniques, such as by dip coating, spray coating, melting processes including extrusion, compression molding and injection molding or a combination of different techniques.

In a representative example of a stepwise procedure, the electrode is first dip-coated with a suitable resorbable polymer or blend of polymers, in particular collagen, gelatin, polyvinyl alcohol and starch, dissolved in a proper solvent. Other polymers can also be used. The thickness of the polymer layer is controlled in manner known to a person skilled in the art. The coating is then subjected to a drying step. The dip coating and drying steps can be done once or can be repeated, depending on required thickness of the final coating. In the next step the polymer is loaded with the drug. The electrode is submerged into a solution containing the drug. The solvent used should be one in which the polymer swells and in which the drug dissolves. After an appropriate contact time, such as from less than a second to 5 min or more, the electrode is removed from the solution and the matrix dried by evaporation of the solvent, possibly under reduced pressure.

In a one-pot procedure the electrode is submerged into a solution of the polymer and the drug of choice in an optimal concentration for a desired coat thickness and, optionally, a desired drug loading. The electrode is then removed from the solution and the solvent evaporated, possibly under reduced pressure.

Alternatively the coating is generated by spray coating, in which a polymer solution optionally containing a drug or a combination of drugs in a suitable solvent is sprayed on the electrode body. The thickness of the coating can be controlled by the number of spraying and drying (evaporation) cycles and the amount of polymer and drug in the solution.

Also comprised by the invention are hydrogel coats of partially hydrolyzed water-soluble polymers such as polyvinyl alcohol, polyacrylic acid and derivatives of polyacrylic acid, e.g., poly (N-isopropylacrylamide). An increase in temperature makes these hydrogels contract, thereby expelling a drug or a combination of drugs incorporated in the coating. Alternatively, the temperature-sensitive hydrogel is an interpenetrating hydrogel network of poly(acrylamide) and poly (acrylic acid), and the increase in temperature causes the hydrogel to swell, thereby allowing the drug to diffuse out of the gel.

Also comprised by the invention is the use of a polymer or a polymer blends for electrically triggered release, such as polyvinyl alcohol/chitosan.

Electrode bundles and arrays of electrodes and electrode bundles of the invention can be embedded in a matrix in substantially the same manner as described above for single electrodes.

Uses

The invention also relates to the use of the matrix-embedded electrode, the matrix-embedded electrode bundle or the array of matrix-embedded electrode bundles for long-lasting nerve stimulation, multi-channel recordings of electrical neuronal activity and levels of transmitter substance through measurements of redox reactions and lesions of the tissue for scientific, medical and animal care purposes.

According to a preferred aspect of the invention the microelectrode, the microelectrode bundle, and the array of microelectrodes or microelectrode bundles of the invention is used in a patient or animal for: recording signals from neurons remaining after brain and/or spinal damage; stimulating neurons to compensate for lost functions; providing pain relief by stimulation of analgesic brain stem centres; providing relief or decrease of tremor and other motor symptoms in Parkinson's disease; relief or decrease of choreatic and other involuntary movements by stimulation within the basal ganglia or associated nuclei; boosting memory by stimulation of cholinergic and/or monoaminergic nuclei in case of Alzheimer's disease or other degenerative disease; control of mood, aggression, anxiety, phobia, affect, sexual over-activity, impotence, eating disturbances by stimulation of limbic centres or other brain areas; providing rehabilitation after stroke or damage of the brain and/or spinal cord by stimulation of remaining connections in the cortex cerebri or descending motor pathways; providing re-establishment of control of spinal functions such as bladder and bowel emptying after spinal cord injury by stimulating relevant parts of the spinal cord; providing control of spasticity by stimulation of inhibitory supraspinal descending centres or appropriate cerebellar areas; providing re-establishment of somatosensory, auditory, visual, olfactory senses by stimulation of relevant nuclei in the spinal cord and the brain.

According to another preferred aspect of the invention the microelectrode, the microelectrode bundle, and the array of microelectrodes or microelectrode bundles of the invention is used in a patient or animal for combined monitoring and stimulation, in particular for: monitoring of epileptic attacks by electrodes implanted into the epileptic focus coupled to a system for delivering antiepileptic drugs or electrical pulses; compensating for a lost connection in the motor system by recording central motor commands, followed by stimulating executive parts of the motor system distal to a lesions; recordings of blood glucose levels to control the hormone release.

According to a further preferred aspect of the invention the microelectrode, the microelectrode bundle, and the array of microelectrodes or microelectrode bundles of the invention is used in a patient or animal for locally lesioning tissue, in particular tumour or abnormally active or epileptogenic nervous tissue by passing current of sufficient magnitude through said electrode, electrode bundle or array of electrode bundles.

In biomedical research, use of the microelectrode, the microelectrode bundle, and the array of microelectrodes or microelectrode bundles of the invention can be used for studying normal and pathological functions of the brain and spinal cord, in particular over a long time.

In a patient having a neuroprosthetic device, the microelectrode, the microelectrode bundle, and the array of microelectrodes or microelectrode bundles of the invention can be used to form an interface between a nerve and said device.

In a patient or an animal, the microelectrode, the microelectrode bundle, and the array of microelectrodes or microelectrode bundles of the invention can be used for controlling the function of an endocrine or exocrine organ, such as in controlling hormone secretion.

In a patient or animal, the microelectrode, the microelectrode bundle, and the array of microelectrodes or microelectrode bundles of the invention can be used for controlling the function of one or more skeletal muscles or a heart muscle.

What is claimed is:

1. Medical microelectrode for implantation into soft tissue of a person or animal resistant to displacement in the tissue by inertia, the electrode having a front end, a rear end and a density at 20° C. of from 0.80 to 1.15, in particular from 0.90 to 1.07, more particularly from 0.95 to 1.03, comprising any of:
    an electrically conductive tubiform lead comprising a metal and/or an electrically conductive polymer, the lead having an outer face and a sealed lumen;
    an electrically conductive wire lead comprising a metal and/or an electrically conductive polymer, the lead having a surface and a buoyant element of a density of less than 1.0 attached to the surface;
    wherein a portion of the outer surface or the surface, respectively, is electrically insulated.

2. The electrode of claim 1, wherein the density is 0.99±0.02.

3. The electrode of claim 1, wherein the lumen is void.

4. The electrode of claim 1, wherein the lumen comprises one or more sections filled with filler and optionally one or more void sections.

5. The electrode of claim 4, wherein the density of the filler is 0.8 or less, in particular 0.6 or less.

6. The electrode of claim 4, wherein the filler comprises a porous material.

7. The electrode of claim 4, wherein the filler comprises a polymer.

8. The electrode of claim 7, wherein the polymer is flexible, in particular resiliently flexible.

9. The electrode of claim 7, wherein the polymer comprises closed pores.

10. The electrode of claim 9, wherein the density at 20° C. of the polymer is less than 0.8, preferably less than 0.6.

11. The electrode of claim 1, wherein the buoyant element comprises a polymer comprising closed pores.

12. The electrode of claim 11, wherein the density at 20° C. of the polymer is less than 0.8, preferably less than 0.6.

13. The electrode of claim 11, wherein the polymer is flexible, in particular resiliently flexible.

14. The electrode of claim 1, fully or partially embedded in a matrix dissolvable or degradable in a body fluid.

15. The electrode of claim 1, comprising an electronic amplifying means and/or a microprocessor means, with the proviso that the combination of electrode and electronic amplifying/microprocessor means has a density at 20° C. of from 0.80 to 1.15, in particular from 0.90 to 1.07, more particularly from 0.95 to 1.03.

16. The electrode of claim 15, wherein the density is 0.99±0.02.

17. The electrode of claim 15, wherein the electronic amplifying/microprocessor means is disposed at or near the rear end.

18. The electrode of claim 1 attached at or near its rear end to an ultra-thin insulated wire for electric communication with an electronic amplifying/microprocessor means disposed at a distance therefrom.

19. The electrode of claim 18, wherein the ultra-thin insulated wire is integral with the electrode wire.

20. The electrode of claim 15, wherein said electronic amplifying/microprocessor is disposed in soft tissue of said person or animal.

21. The electrode of claim 15, wherein said electronic amplifying/microprocessor comprises a source of electric energy.

22. The electrode of claim 15, wherein said electronic amplifying/microprocessor comprises a transmitter and/or receiver transmitting and/or receiving radiation to/from a control unit disposed externally of said patient or animal.

23. The electrode of claim 1, comprising anchoring means disposed at or near its front end.

24. An electrode bundle comprising two or more electrodes of claim 1.

25. The electrode bundle of claim 24 partially or fully enclosed in a material dissolvable or degradable in a body fluid.

26. An electrode array comprising two or more electrodes of claim 1.

27. The electrode array of claim 26 partially or fully enclosed in a material dissolvable or degradable in a body fluid.

28. The electrode array of claim 27 partially or fully enclosed in a material dissolvable or degradable in a body fluid.

29. The electrode of claim 1, further comprising a sealed porous material.

30. An electrode array comprising two or more electrode bundles of claim 24.

* * * * *